US012194318B2

(12) United States Patent
Gong et al.

(10) Patent No.: US 12,194,318 B2
(45) Date of Patent: Jan. 14, 2025

(54) RADIATION IRRADIATION SYSTEM

(71) Applicant: NEUBORON THERAPY SYSTEM LTD., Fujian (CN)

(72) Inventors: Qiu-ping Gong, Fujian (CN); Wei-lin Chen, Fujian (CN)

(73) Assignee: NEUBORON THERAPY SYSTEM LTD., Xiamen (CN)

( * ) Notice: Subject to any disclaimer, the term of this patent is extended or adjusted under 35 U.S.C. 154(b) by 329 days.

(21) Appl. No.: 17/836,017

(22) Filed: Jun. 9, 2022

(65) Prior Publication Data

US 2022/0296931 A1    Sep. 22, 2022

Related U.S. Application Data

(63) Continuation of application No. PCT/CN2020/125833, filed on Nov. 2, 2020.

(30) Foreign Application Priority Data

Dec. 24, 2019 (CN) .......................... 201911343833.7

(51) Int. Cl.
*A61N 5/10* (2006.01)
(52) U.S. Cl.
CPC ...... *A61N 5/1083* (2013.01); *A61N 2005/109* (2013.01); *A61N 2005/1098* (2013.01)
(58) Field of Classification Search
CPC ............ A61N 5/1083; A61N 2005/109; A61N 2005/1098
See application file for complete search history.

(56) References Cited

U.S. PATENT DOCUMENTS

2005/0234327 A1    10/2005   Saracen et al.
2010/0237257 A1    9/2010    Saracen et al.
(Continued)

FOREIGN PATENT DOCUMENTS

CN    101217913 A    7/2008
CN    102256562 A    11/2011
(Continued)

OTHER PUBLICATIONS

International Search Report of PCT/CN2020/125833, Jan. 27, 2021.
European Patent Office, "Office Action", Dec. 21, 2023, Germany.

*Primary Examiner* — Nicole M Ippolito
(74) *Attorney, Agent, or Firm* — Locke Lord LLP; Tim Tingkang Xia, Esq.

(57) ABSTRACT

A radiation irradiation system including a radiation generating device and a carrying table, a beam generated by the radiation generating device irradiates an irradiated object on the carrying table, the radiation irradiation system further includes a carrying table positioning device, the carrying table is supported by the carrying table positioning device, the carrying table positioning device includes a positioning mechanism, the positioning mechanism includes a linear axis, the carrying table positioning device may horizontally move along the linear axis, and an extending direction of the linear axis is parallel to an irradiation direction of beams generated by the radiation generating device. In the positioning process of the carrying table, most of the carrying table positioning device is located in the space between the linear axis and the beam outlet, the radioactivity and lifespan shortening caused by the radiation of the various components of the carrying table positioning device are reduced.

17 Claims, 4 Drawing Sheets

(56) References Cited

U.S. PATENT DOCUMENTS

2011/0066278 A1    3/2011  Pinault et al.
2015/0327818 A1   11/2015  Buck et al.
2019/0167212 A1*   6/2019  Pinault ................. A61N 5/1049

FOREIGN PATENT DOCUMENTS

| CN | 103764039 A  | 4/2014  |
| CN | 109464749 A  | 3/2019  |
| CN | 109464751 A  | 3/2019  |
| CN | 109561872 A  | 4/2019  |
| CN | 211675930 U  | 10/2020 |
| EP | 2921206 A1   | 9/2015  |
| JP | 2003190137 A | 7/2003  |
| JP | 2014161623 A | 9/2014  |
| JP | 2015173947 A | 10/2015 |
| JP | 2017176354 A | 10/2017 |
| JP | 2018108342 A | 7/2018  |
| JP | 2019524322 A | 9/2019  |
| TW | 201249405 A  | 12/2012 |
| WO | 2013016759 A1 | 2/2013 |
| WO | 2018028901 A1 | 2/2018 |
| WO | 2018159565 A1 | 9/2018 |

\* cited by examiner

RADIATION IRRADIATION SYSTEM

CROSS-REFERENCE TO RELATED PATENT APPLICATION

This application is a continuation application of International Application No. PCT/CN2020/125833, filed on Nov. 2, 2020, which claims priority to Chinese Patent Application No. 201911343833.7, filed on Dec. 24, 2019, the disclosures of which are hereby incorporated by reference.

FIELD

The present disclosure relates to a radiation irradiation system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

With the development of atomic science, radiotherapy such as Cobalt-60, a linear accelerator, an electron beam etc., has become one of the main means for cancer treatment. However, conventional photon or electron therapy is limited by physical conditions of a radiation itself, it may not only kill tumor cells, but also damage a large number of normal tissues in a beam path. In addition, due to different sensitivities of the tumor cells to the radiation, conventional radiotherapy is often less effective in the treatment of malignant tumors with high irradiation resistance (such as glioblastoma multiforme and melanoma).

In order to reduce the irradiation damage to the normal tissues around the tumors, a concept of target therapy in chemotherapy has been applied to the radiotherapy. For the tumor cells with high irradiation resistance, an irradiation source with high relative biological effectiveness (RBE) is also actively developed at present, such as proton therapy, heavy particle therapy, neutron capture therapy, etc. The neutron capture therapy combines the above two concepts, such as boron neutron capture therapy, and provides a better choice of cancer treatment than conventional radiation by means of specific agglomeration of a boron-containing medicine in the tumor cells in combination with accurate neutron beam regulation.

During the radiotherapy, the beam is aligned with the tumor cells in an irradiated object on a treatment table through a treatment table positioning device, so as to implement accurate treatment while minimize the irradiation damage to the normal tissues around the tumor cells in the irradiated object. During the neutron capture therapy, the treatment table positioning device is in a mixed irradiation field of neutrons and gamma rays, which is easy to be activated by neutrons to produce secondary irradiation, and the service life is reduced due to the irradiation damage.

Therefore, it is necessary to propose a new technical solution to solve the above problems.

SUMMARY

In order to solve the above problems, the present disclosure provides a radiation irradiation system which may include a radiation generating device and a carrying table, a beam generated by the radiation generating device irradiates an irradiated object on the carrying table, the radiation irradiation system further includes a carrying table positioning device supporting the carrying table and including a positioning mechanism, the positioning mechanism includes a linear axis along which the carrying table positioning device is horizontally movable and an extending direction of which is parallel to an irradiation direction of the beam generated by the radiation generating device. During the process of positioning the carrying table, the whole carrying table positioning device moves in a direction parallel to the irradiation direction of the beam generated by the radiation generating device, and most of the carrying table positioning device is located in a space between the linear axis and a beam outlet, which reduces radioactivity and shortening of service life due to radiation irradiation on components of the carrying table positioning device.

Preferably, the positioning mechanism may further include a robot arm arranged between the linear axis and the carrying table and connecting the carrying table to the linear axis, and the carrying table is movable together with the robot arm along the linear axis.

Furthermore, the radiation irradiation system may further include an irradiation room with a ceiling on which the linear axis is mounted and a floor toward which the whole robot arm extends. The linear axis is directly fixed on the ceiling without an additional linear axis fixing mechanism such as a steel structure gantry, thus reducing the amount of steel in the irradiation room and avoiding secondary radiation due to radiation irradiation on the fixing mechanism.

Furthermore, the linear axis may include a fixed slide rail and a support seat connected with the robot arm and sliding along the slide rail, and a distance between a slide surface of the slide rail and the support seat and a center of a beam outlet of the radiation generating device in a direction perpendicular to the slide surface is less than 2 meters. Enough operating space is provided for the carrying table positioning device to position the carrying table at a required position relative to the beam outlet. Furthermore, the robot arm may include a first arm fixedly connected with the support seat, a second arm pivotally connected with the first arm and defining a first pivot axis, a third arm pivotally connected with the second arm and defining a second pivot axis, a fourth arm pivotally connected with the third arm and defining a third pivot axis, a fifth arm pivotally connected with the fourth arm and defining a fourth pivot axis, a sixth arm pivotally connected with the fifth arm and defining a fifth pivot axis, and a seventh arm pivotally connected with the sixth arm and defining a sixth pivot axis. Furthermore, the seventh arm may be fixedly connected with the carrying table, the second, third and fifth pivot axis are parallel to the slide surface, the fourth pivot axis is perpendicular to the third pivot axis, and the first and sixth pivot axis are perpendicular to the slide surface.

Furthermore, the radiation irradiation system may further include a control device controlling the carrying table positioning device and including a user interface, a system control module and a positioning control module, the user interface is connected with the system control module, and the system control module is connected with the positioning control module.

Furthermore, the system control module may transmit an instruction from the user interface to the positioning control module after receiving the instruction, and the positioning control module controls movement of the positioning mechanism. The positioning control module may be capable of receiving position information of the positioning mechanism and transmitting it to the system control module, and the system control module controls the user interface to indicate the position information of the positioning mechanism. The carrying table positioning device may further include a driving mechanism to drive movement of the linear axis and the robot arm, and the positioning control module is connected with the driving mechanism and controls the driving mechanism. Furthermore, an operating state or data of the driving mechanism may be fed back to the system control module through the positioning control module, the system control module or the positioning control module controls the driving mechanism according to the operating state or data of the driving mechanism, and the system control module may also transmit the operating state or data of the driving mechanism to the user interface for state indication.

Furthermore, a sensor may be arranged on the carrying table or the carrying table positioning device and connected to the system control module, and the system control module receives a signal of the sensor, and then transmits an instruction to the positioning control module to control movement of the carrying table positioning device, and transmits the signal of the sensor to the user interface for state indication. The sensor is an anti-collision sensor arranged on the carrying table or the robot arm, and the anti-collision sensor may be a mechanical sensor, a photoelectric sensor, a radar sensor, an ultrasonic sensor or a laser rangefinder.

Preferably, the radiation irradiation system may be a neutron capture therapy system, the radiation generating device includes a neutron generating device and a beam shaping assembly, wherein the beam shaping assembly is configured to adjust quality of a neutron beam generated by the neutron generating device to a preset value, and the neutron beam generated by the neutron generating device passes through the beam shaping assembly to irradiate the irradiated object on the carrying table.

Furthermore, the neutron generating device may include an accelerator and a target, a charged particle beam generated by acceleration of the accelerator interacts with the target to generate the neutron beam.

Furthermore, the beam shaping assembly may include a reflector, a moderator, a thermal neutron absorber, an radiation shield and a beam outlet, the moderator decelerates neutrons generated from the target to an epithermal neutron energy region, the reflector surrounds the moderator and guides deviated neutrons back to the moderator to improve intensity of an epithermal neutron beam, the thermal neutron absorber is arranged to absorb thermal neutrons to avoid excessive dose for shallow normal tissues during treatment, and the radiation shield is arranged to shield neutrons and photons leaked from parts other than the beam outlet.

According to the radiation irradiation system of the present disclosure, during the process of positioning the carrying table, the whole carrying table positioning device moves in a direction parallel to the irradiation direction of the beam generated by the radiation generating device, and most of the carrying table positioning device is located in a space between the linear axis and a beam outlet, which reduces radioactivity and shortening of service life due to radiation irradiation on components of the carrying table positioning device.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Hereinafter, embodiments of the present invention will be further described in detail with reference to the accompanying drawings, so that those skilled in the art may implement them with reference to the specification.

Figure 1:
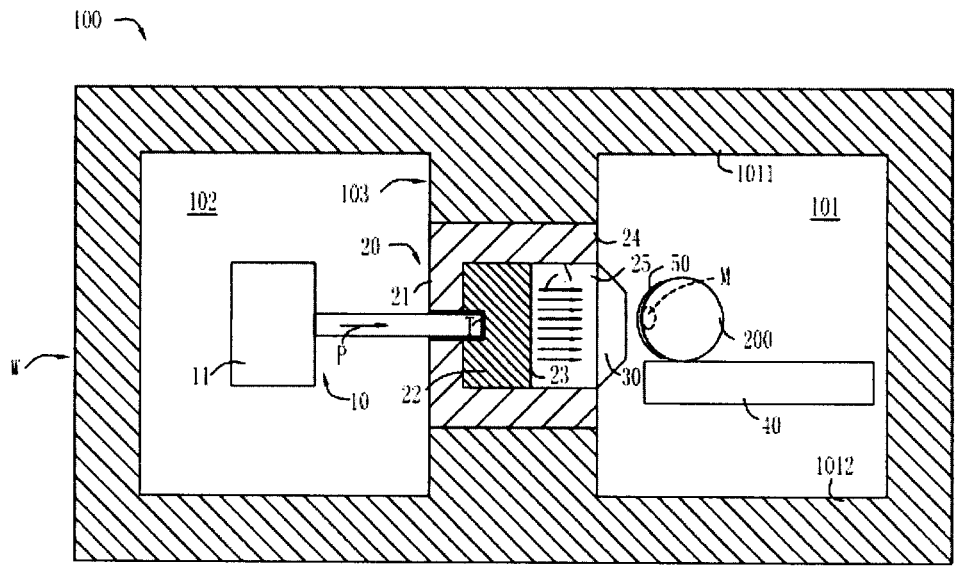
FIG. 1 is a schematic structural diagram of a neutron capture therapy system according to an embodiment of the present disclosure.

As shown in FIG. 1, the radiation irradiation system in the embodiment is preferably a boron neutron capture therapy system 100 which includes a neutron generating device 10, a beam shaping assembly 20, a collimator 30 and a treatment table 40. The neutron generating device 10 includes an accelerator 11 and a target T. The accelerator 11 accelerates charged particles (such as protons, deuterons, etc.) to generate a charged particle beam P such as a proton beam. The charged particle beam P irradiates the target T and interacts with the target T to generate a neutron beam N. The target T is preferably a metal target. A proper nuclear reaction is selected according to characteristics such as required neutron yields and energy, available energy and current for accelerating the charged particles, physicochemical property of the metal target, etc. Nuclear reactions which are often discussed are $^7Li(p, n)^7Be$ and $^9Be(p, n)^9B$, both of which are endothermic reactions. Energy thresholds of the two nuclear reactions are 1.881 MeV and 2.055 MeV, respectively. An ideal neutron source for boron neutron capture therapy is an epithermal neutron with a keV energy level. In theory, when protons with energy only slightly higher than the threshold are used to bombard a target made of metal lithium (Li), neutrons with relatively low-energy may be produced and may be applied to clinical practice without much retard processing. However, the cross-section for interaction of the two targets made of metals Li and beryllium (Be) with protons with the threshold energy is not high, thus protons with higher energy are usually selected to initiate the nuclear reaction, so as to produce enough neutron flux. An ideal target shall have characteristics such as high neutron yields, generated neutron energy distribution close to an epithermal neutron energy region (which will be described in detail below), few generation of strongly penetrating irradiation, safety, low cost, easy operation, high temperature resistance, etc. However, in practice, the nuclear reaction meeting all requirements may not be found. In the embodiments of the present disclosure, the target made of metal Li is used. However, it is well known to those skilled in the art that the material of the target T may also be made of metal materials other than Li and Be, such as tantalum (Ta) or tungsten (W), etc. The target T may be formed in the shape of a circular plate, in another solid shape, or a liquid (liquid metal). The accelerator 11 may be a linear accelerator, a cyclotron, a synchrotron, or a synchrocyclotron. The neutron generating device 10 may also be a nuclear reactor rather than using the accelerator and the target. No matter the neutron source of the boron neutron capture therapy comes from the nuclear reactor or the nuclear reaction between the charged particles of the accelerator and the target, what generated is actually a mixed irradiation field, that is, the beam contains neutrons and photons with energy from low energy to high energy. For the boron neutron capture therapy of deep tumors, the more the amount of radiations except epithermal neutrons are, the larger the proportion of non-selective dose deposition in normal tissues is, thus those radiations which may cause unnecessary doses shall be reduced as much as possible. In addition, for normal tissues of an irradiated object, excessive radiations which also cause unnecessary dose deposition shall be avoided.

The neutron beam N generated by the neutron generating device 10 passes through the beam shaping assembly 20 and the collimator 30 in sequence to irradiate the irradiated object 200 on the treatment table 40. The beam shaping assembly 20 may adjust the beam quality of the neutron beam N generated by the neutron generating device 10, and the collimator 30 is arranged to converge the neutron beam N, so that the neutron beam N has higher targeting in the treatment process. The positions of the treatment table 40 and the irradiated object 200 may also be adjusted to align the beam with the tumor cell M in the irradiated object 200. The adjustment may be manually operated or automatically implemented through a series of control mechanisms (which are detailed below). It should be understood that the present disclosure may not have the collimator, and the beam coming out of the beam shaping assembly 20 directly irradiates the irradiated object 200 on the treatment table 40.

The beam shaping assembly 20 further includes a reflector 21, a moderator 22, a thermal neutron absorber 23, a radiation shield 24 and a beam outlet 25. Since the neutrons generated by the neutron generating device 10 have a wide energy spectrum, it is necessary to reduce the amount of other kinds of neutrons and photons as much as possible except the epithermal neutrons meeting treatment requirements, so as to avoid harm to an operator or the irradiated object. Therefore, the neutrons coming out of the neutron generating device 10 are required to pass through the moderator 22, so as to adjust energy (>40 kev) of fast neutrons therein to the epithermal neutron energy region (0.5 eV-40 keV) and reduce the thermal neutrons (<0.5 ev) as much as possible. The moderator 22 is made of a material with a large cross-section for interaction with the fast neutrons and a small cross-section for interaction with the epithermal neutrons. As a preferable embodiment, the moderator 22 is made of at least one of $D_2O$, $AlF_3$, Fluental™, $CaF_2$, $Li_2CO_3$, $MgF_2$ or $Al_2O_3$. The reflector 21 surrounds the moderator 22 and reflects the neutrons passing through the moderator 22 and diffused around back to the neutron beam N to improve the utilization of the neutrons, and the reflector 21 is made of a material with strong neutron reflection capability. As a preferable embodiment, the reflector 21 is made of at least one of Plumbum (Pb) or Nickel (Ni). The thermal neutron absorber 23 is arranged at the rear of the moderator 22 and is made of a material with a large cross-section for interaction with the thermal neutrons. As a preferable embodiment, the thermal neutron absorber 23 is made of Li-6, and the thermal neutron absorber 23 is arranged to absorb the thermal neutrons passing through the moderator 22 to reduce the amount of the thermal neutrons in the neutron beam N, so as to avoid excessive doses for shallow normal tissues during treatment. It should be understood that the thermal neutron absorber may be integrated with the moderator. The material of the moderator contains Li-6. The radiation shield 24 is arranged to shield neutrons and photons leaked from parts other than the beam outlet 25. The material of the radiation shield 24 includes at least one of a photon shielding material or a neutron shielding material. As a preferable embodiment, the material of the radiation shield 24 includes Pb as the photon shielding material and polyethylene (PE) as the neutron shielding material. The collimator 30 is arranged at the rear of the beam outlet 25. The epithermal neutron beam coming out of the collimator 30 irradiates the irradiated object 200 and is retarded into the thermal neutrons after passing through the shallow normal tissues, to reach the tumor cell M. It should be understood that the beam shaping assembly 20 may also have other configurations as long as the epithermal neutron beam required for treatment may be acquired. For the convenience of description, when the collimator 30 is provided, an outlet of the collimator 30 may also be considered as the beam outlet 25 described below.

After the irradiated object 200 takes or is injected with a boron-containing (B-10) medicine, the boron-containing medicine is selectively aggregated in the tumor cell M, and then by utilizing the characteristics that the boron-containing (B-10) medicine has a high capture cross-section on the thermal neutrons, two heavily charged particles of $^4$He and $^7$Li are generated by means of the $^{10}$B(n, α)$^7$ Li neutron capture and a nuclear fission reaction. An average energy of the two charged particles is about 2.33 MeV, which has the characteristics of high Linear Energy Transfer (LET) and short range. The LEF and range of α particle are 150 keV/μm and 8 μm, respectively, while those of $^7$Li heavily charged particle are 175 keV/μm and 5 μm, respectively. The total range of the two particles is about the size of a cell, thus the irradiation damage to an organism may be limited at the cell level, so as to achieve the purpose of locally killing the tumor cells without too much damage to the normal tissues.

In the embodiment, a radiation shielding device 50 is further arranged between the irradiated object 200 and the beam outlet 25 to shield the irradiation of the beam coming out of the beam outlet 25 to the normal tissues of the irradiated object. It should be understood that the radiation shielding device 50 may also not be arranged. The whole boron neutron capture therapy system 100 is housed in a concrete building. Specifically, the boron neutron capture therapy system 100 further includes an irradiation room 101 and a charged particle beam generating room 102. The irradiated object 200 on the treatment table 40 experiences neutron beam N irradiation therapy in the irradiation room 101. The charged particle beam generating room 102 at least partially houses the accelerator 11. The beam shaping assembly 20 is at least partially housed in a partition wall 103 between the irradiation room 101 and the charged particle beam generating room 102. It should be understood that the partition wall 103 may completely separate the irradiation room 101 from the charged particle beam generating room 102, or the partition wall 103 may also partially separate the irradiation room 101 from the charged particle beam generating room 102, so that the irradiation room 101 and the charged particle beam generating room 102 are in communication with each other. There may be one or more targets T. The charged particle beam P may selectively interact with one or more targets T or simultaneously interact with multiple targets T, to generate one or more therapeutic neutron beams N. Corresponding to the number of the targets T, there may be one or more beam shaping assemblies 20, collimators 30 and treatment tables 40. Multiple treatment tables may be arranged in the same irradiation room, or each of the treatment tables may be configured with a separate irradiation room. The irradiation room 101 and the charged particle beam generating room 102 are a space defined by surrounding of a concrete wall W (including the partition wall 103), and a concrete structure may shield neutrons and other radiations leaked during the operation of the boron neutron capture therapy system 100. The boron neutron capture therapy system 100 may also include a preparation room, a control room and other spaces (not shown) for assisting in therapy. Each irradiation room may be configured with a preparation room for fixing the irradiated object to the treatment table, injecting the boron-containing medicine, simulating a treatment plan, and other preparation work before irradiation therapy. A connecting channel is arranged between the preparation room and the irradiation room, through which the irradiated object is directly pushed into the irradiation room or controlled by a control mechanism to automatically enter the irradiation room through a track, after the preparation work is completed. The control room is arranged to control the accelerator, a beam transmission part, a treatment table positioning device, etc. Control and management are applied to the whole irradiation process. A manager may also monitor multiple irradiation rooms simultaneously in the control room.

The position adjustment of the treatment table 40 and the irradiated object 200 will be described in detail below with reference to FIGS. 2-6.

Figure 2:
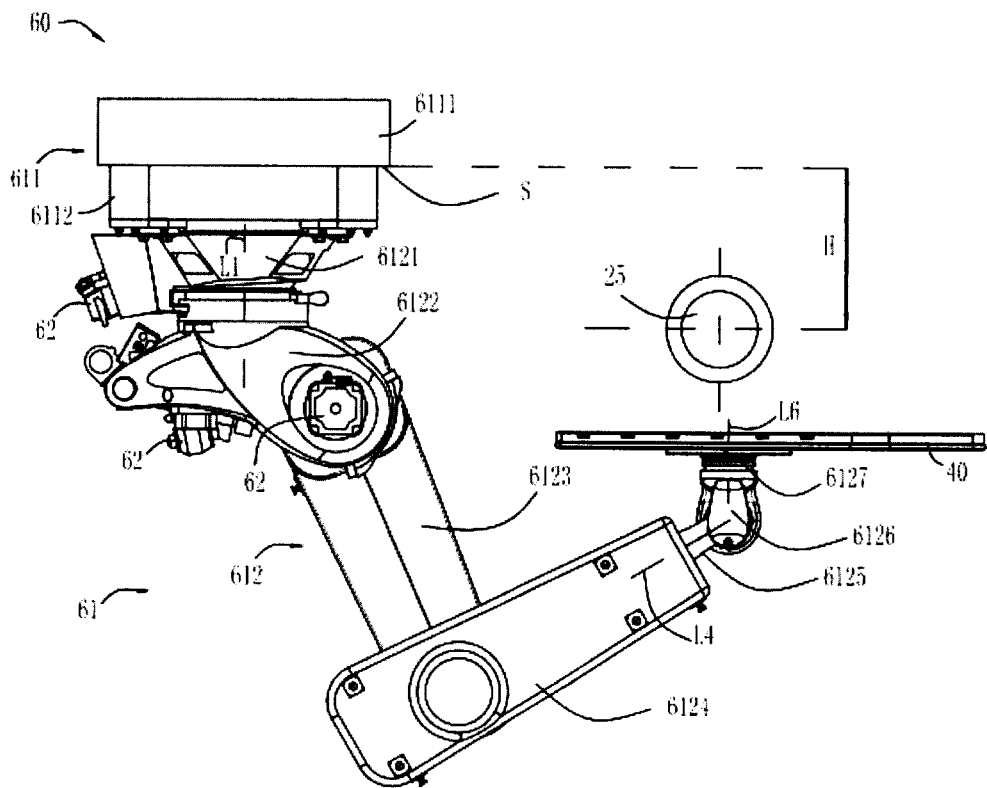
FIG. 2 is a schematic structural diagram of a treatment table positioning device of a neutron capture therapy system according to an embodiment of the present disclosure.
Figure 3:
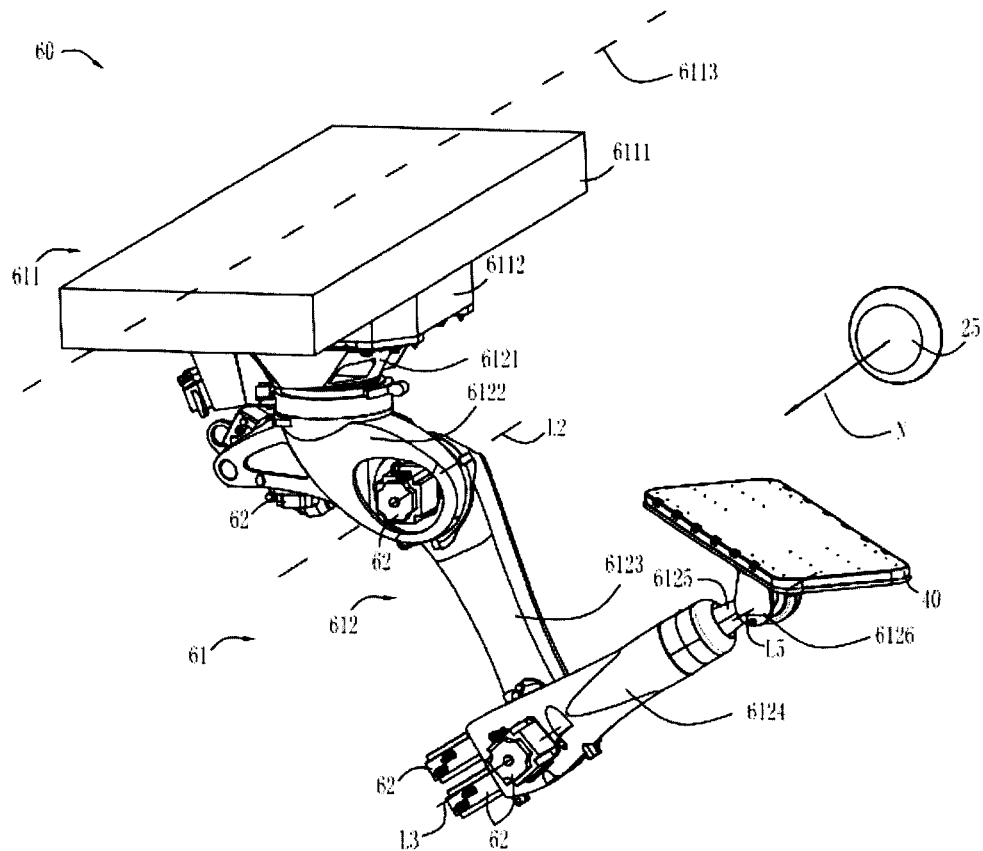
FIG. 3 is a schematic diagram of FIG. 2 in another direction.

The neutron capture therapy system 100 further includes a treatment table positioning device 60 and a control device 70. The treatment table 40 is supported by the treatment table positioning device 60, and the control device 70 controls the treatment table positioning device 60. As shown in FIGS. 2 and 3, in an embodiment, the treatment table positioning device 60 includes a positioning mechanism 61. The positioning mechanism 61 includes a linear axis 611 and a robot arm 612. The robot arm 612 is arranged between the linear axis 611 and the treatment table 40. The treatment table 40 is connected to the linear axis 611, and the treatment table 40 is movable together with the robot arm 612 along the linear axis 611. In the embodiment, the linear axis 611 is mounted on a ceiling 1011 of the irradiation room 101, and the whole robot arm 612 extends toward a floor 1012 of the irradiation room 101. It should be understood that the linear axis 611 may also be mounted on other surfaces, such as a wall or a floor. The linear axis 611 is configured as a slide rail 6111 fixed to the ceiling 1011 and a support seat 6112 connected with the robot arm 612, and the support seat 6112 slides along the slide rail 6111. It should be understood that other configurations may also be possible. The linear axis is directly fixed on the ceiling 1011 without an additional linear axis fixing mechanism such as a steel structure gantry, thus reducing the amount of steel in the irradiation room and avoiding secondary radiation due to activation of the fixing mechanism by the neutrons. The robot arm 612 is a multi-axis robot arm connecting the support seat 6112 with the treatment table 40. In the embodiment, the robot arm includes a first arm 6121 fixedly connected with the support seat 6112, a second arm 6122 pivotally connected with the first arm 6121 and defining a first pivot axis L1, a third arm 6123 pivotally connected with the second arm 6122 and defining a second pivot axis L2, a fourth arm 6124 pivotally connected with the third arm 6123 and defining a third pivot axis L3, a fifth arm 6125 pivotally connected with the fourth arm 6124 and defining a fourth pivot axis L4, a sixth arm 6126 pivotally connected with the fifth arm 6125 and defining a fifth pivot axis L5, and a seventh arm 6127 pivotally connected with the sixth arm 6126 and defining a sixth pivot axis L6. The seventh arm 6127 is fixedly connected with the treatment table 40. The treatment table positioning device 60 further includes a driving mechanism 62 to drive movement of the linear axis 611 and the robot arm 612. The control device 70 controls the driving mechanism 62. The driving mechanism 62, such as a motor, drives the second arm 6122 to the seventh arm 6127 to pivot around the pivot axis L1-L6, and the support seat 6112 and the first arm 6121 fixedly connected with the support seat 6112 move along the slide rail 6111, thereby positioning the treatment table 40 to a required position. An extending direction 6113 of the linear axis 611 is parallel to a direction of the neutron beam N coming out of the beam outlet 25 to the irradiated object on the treatment table 40, so that during the process of positioning the treatment table, the whole robot arm 612 moves in a direction parallel to the direction of the neutron beam N. Most of the robot arm is located in a space between the slide rail and a neutron beam outlet, which reduces radioactivity and shortening of service life due to activation of components of the robot arm by the neutrons. A distance H between a slide surface S of the slide rail 6111 and the support seat 6112 and a center of the beam outlet 25 in a direction perpendicular to the slide surface S is less than 2 meters, which provides enough operating space for the treatment table positioning device 60 to position the treatment table 40 at a required position relative to the beam outlet 40. In the embodiment, the slide surface S is parallel to the plane where the ceiling is located, the second pivot axis L2, the third pivot axis L3 and the fifth pivot axis L5 are parallel to the slide surface S, the fourth pivot axis L4 is perpendicular to the third pivot axis L3, and the first pivot axis L1 and the sixth pivot axis L6 are perpendicular to the slide surface S, so that the treatment table 40 is always kept parallel to the ceiling 1011 or the floor 1012. It should be understood that other arrangement may also be possible. The fifth arm 6125, the sixth arm 6126 and the seventh arms 6127 form wrist of the robot arm 612, to adjust an inclination angle of the treatment table 40 around the fifth pivot axis L5 and a rotation angle of the treatment table 40 around the fourth pivot axis L4 and the sixth pivot axis L6. The first arm 6121 to the fourth arm 6124 and the linear axis 611 adjust the spatial coordinate position of the whole treatment table 40. It should be understood that the treatment table positioning device 60 may have other configuration, for example, it does not include the linear axis 611 or the robot arm 612 includes more or less arms.

Figure 4:
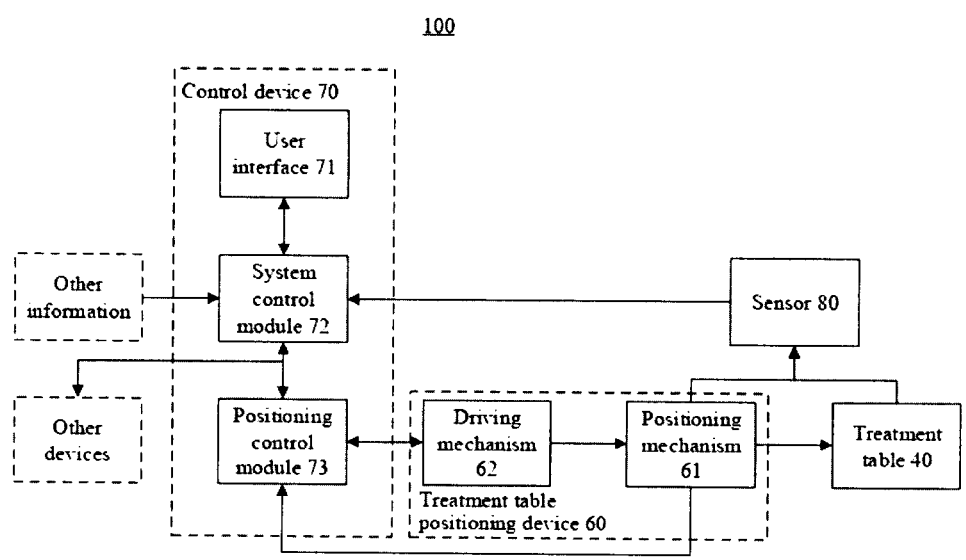
FIG. 4 is a schematic module diagram of a neutron capture therapy system according to an embodiment of the present disclosure.

A sensor 80 may be arranged on the treatment table 40 or the treatment table positioning device 60. As shown in FIG. 4, the sensor 80 is arranged on the positioning mechanism 61 and the treatment table 40. In an embodiment, the sensor 80 is an anti-collision sensor arranged on the treatment table 40 and the robot arm 612. When an edge of the treatment table or the robot arm touches another object or another object is present within a setting range of the sensor, the sensor is triggered to generate a signal and transmit the signal to the control device 70. The control device 70 controls the driving mechanism 62 to stop driving movement of the positioning mechanism 61. That is, the treatment table 40 is controlled to stop moving. The anti-collision sensor may be a mechanical sensor, a photoelectric sensor, a radar sensor, an ultrasonic sensor, a laser rangefinder, etc. It should be understood that the anti-collision sensor may also generate a human body sensible signal, and an operator may manually control the driving mechanism to stop driving according to the sensible signal. Instead of controlling the treatment table to stop moving, another safe operation may be implemented, such as making reverse movement before collision. More specifically, the mechanical sensor may be arranged at the peripheral edge of the treatment table 40 and outer shells of the third arm 6123 and the fourth arm 6124 of the robot arm 612. For example, an elastic protective cover is arranged at a corresponding position, and an electronic switching device is arranged in the protective cover. The electronic switching device is triggered to generate a signal when the protective cover experiences collision during movement. Or, a laser radar sensor is mounted on the back of the treatment table 40, set with a radar scanning range, and generate a signal when another object is scanned to be present within the specified range. It should be understood that the anti-collision sensor may also be arranged at another position.

The control device 70 includes at least one user interface 71 that allows the operator to interactively participate in controlling the treatment table positioning device 60. The control device 70 also includes a system control module 72 and a positioning control module 73. The user interface 71 is connected with the system control module 72. The system control module 72 is connected with the positioning control module 73. The positioning control module 73 is connected with the driving mechanism 62 and controls the driving mechanism 62. The system control module 72 transmits an instruction from the user interface 71 to the positioning control module 73 after receiving the instruction, and the positioning control module 73 automatically controls movement of the positioning mechanism 61. Position information of the positioning mechanism 61 may be fed back to the system control module 72 through the positioning control module 73 and transmitted to the user interface 71 for state indication. An operating state or data of the driving mechanism 62 is also fed back to the system control module 72 through the positioning control module 73. The system control module 72 or the positioning control module 73 controls the driving mechanism 62 according to the information. The system control module 72 may also transmit the information to the user interface 71 for state indication. The sensor 80 is also connected to the system control module 72. After receiving a signal of the sensor 80, the system control module 72 transmits an instruction to the positioning control module 73 to control movement of the treatment table positioning device 60, and transmits the signal of the sensor 80 to the user interface 71 for state indication. It should be understood that the system control module 72 and the positioning control module 73 may be integrated together, and may have other hardware configuration.

In an embodiment, the user interface 71 includes a fixed controller 711, a hand-held controller 712 and a man-machine interaction control interface 713 which are arranged to control movement of the treatment table positioning device 60 and the treatment table 40 inside and outside the irradiation room. The fixed controller 711 is fixed on the wall or another position of the irradiation room 101.

Figure 5:
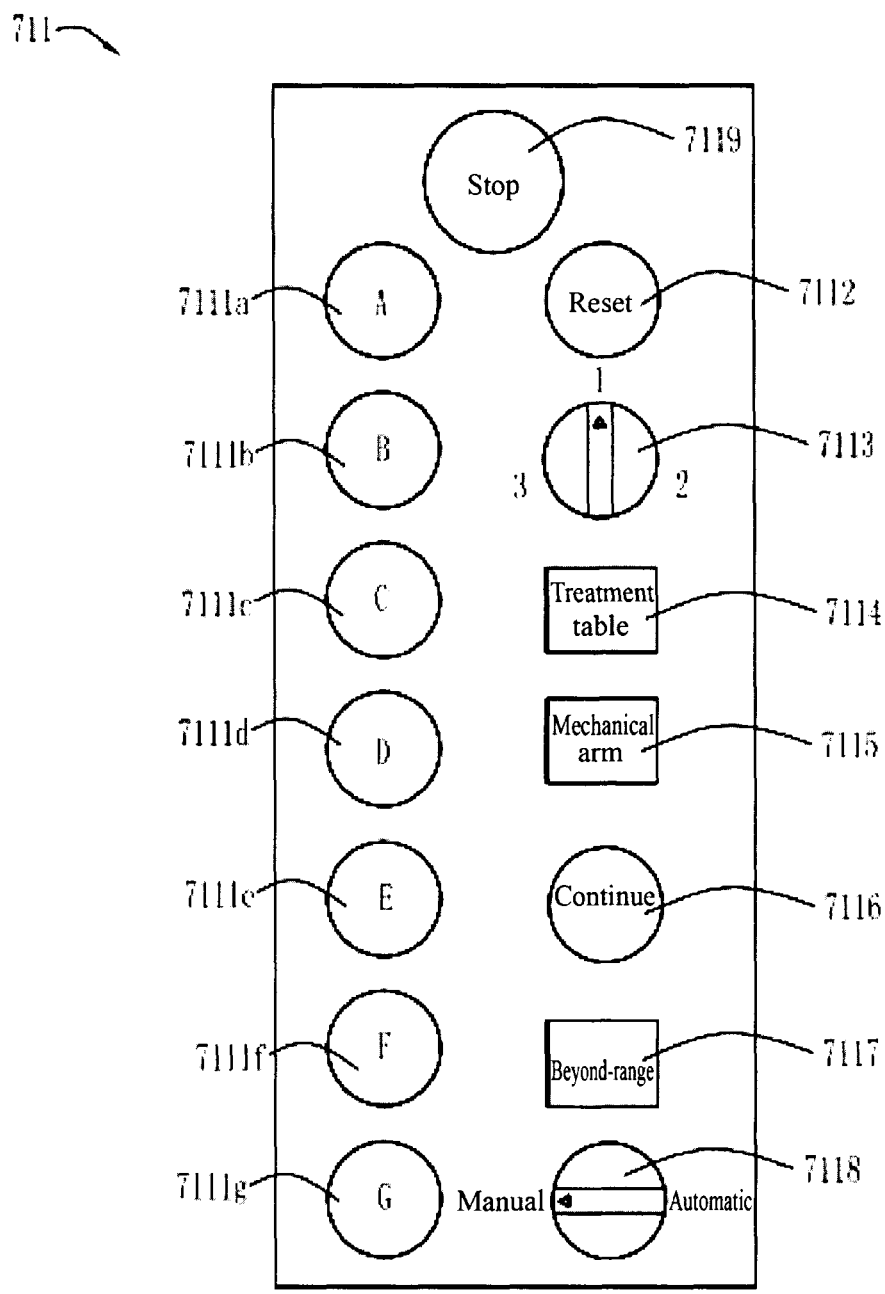
FIG. 5 is a schematic diagram of a user interface of a fixed controller of a control device of a neutron capture therapy system according to an embodiment of the present disclosure.

As shown in FIG. 5, the fixed controller 711 is provided with seven preset position buttons which are arranged to control the treatment table 40 to automatically run to a simulated preset position where a to-be-irradiated part of the irradiated object faces the beam outlet 25, and which are shown respectively as: a preset position A (left face, facing the beam outlet, i.e., the left face is perpendicular to the direction of the neutron beam N) button 7111*a*, a preset position B (right face, facing the beam outlet, i.e., the right face is perpendicular to the direction of the neutron beam N) button 7111*b*, a preset position C (30 degrees to the left, the angle between the left face and the direction of the neutron beam N is 60 degrees) button 7111*c*, a preset position D (60 degrees to the left, the angle between the left face and the direction of the neutron beam N is 30 degrees) button 7111*d*, a preset position E (the top of the head, facing the beam outlet, i.e., the left and right faces are parallel to the direction of the neutron beam N) button 7111*e*, a preset position F (30 degrees to the right, the angle between the right face and the direction of the neutron beam N is 60 degrees) button 7111*f*, and a preset position G (60 degrees to the right, the angle between the right face and the direction of the neutron beam N is 30 degrees) button 7111*g*. The preset position buttons may be provided with indicator lights, respectively. When the treatment table 40 runs in place, the position information of the positioning mechanism 61 (coordinate of a preset reference point on the treatment table 40) is fed back to the positioning control module 73. The positioning control module 73 transmits the information to the system control module 72. The system control module 72 controls a corresponding preset position button to emit light as a prompt, so as to prevent the operator from mistakenly considering 'in place' affecting the positioning accuracy. It should be understood that another preset position button may also be arranged as required, or preset position buttons of which positions have been set may be reset in the control device. The fixed controller 711 is also provided with a reset button 7112, a treatment table movement speed switching button 7113, a treatment table collision sensor triggering indicator light 7114 and a robot arm collision sensor triggering indicator light 7115, a continue-to-operate button with elimination of triggering a collision 7116, a beyond-range indicator light 7117, a manual/automatic switching button 7118, and an emergency stop button 7119. The reset button 7112 is arranged to control the treatment table 40 to automatically run to an initial position of the irradiated object 200 to be lied on the treatment table 40. The treatment table movement speed switching button 7113 is arranged to set speed levels of the treatment table 40, the positioning control module 73 automatically controls the operating speed of the driving mechanism 62 according to the levels. As to the treatment table collision sensor triggering indicator light 7114 and a robot arm collision sensor triggering indicator light 7115, when the treatment table 40 or the robot arm 611 collides, the sensor 80 is triggered to transmit a signal, and the system control module 72 transmits an instruction to the positioning control module 73 after receiving the signal, to control the treatment table positioning device 60 to stop moving or stop after reverse movement before collision occurs, and control a corresponding indicator light to emit light for state indication, and at the moment, the operator is unable to control the treatment table to continue its movement through the control device. As to the continue-to-operate button with elimination of triggering a collision 7116, when the treatment table collision sensor triggering indicator light 7114 or the robot arm collision sensor triggering indicator 7115 emit light and the treatment table positioning device 60 stops moving, the operator manually eliminates the collision and controls the indicator lights 7114 and 7115 to stop emitting light, and at the moment, when the continue-to-operate button 7116 is pressed, the treatment table positioning device 60 continues to move to a preset position or an initial position, or the operator may continue to control movement of the treatment table through another user interface. As to the beyond-range indicator light 7117, the control device 70 simulates the operating range of the treatment table 40 and the treatment table positioning device 60 in the irradiation room 101, for example, simulates a safe operating space with the wall, ceiling, floor and outline of collimator of the irradiation room, when the treatment table is manually controlled in a manual mode (detailed below) to move, and when coordinate of the preset reference point on the treatment table 40 exceeds the simulated operating range, information of exceeding the range is fed back to the positioning control module 73, the positioning control module 73 transmits the information to the system control module 72, and the system control module 72 controls the beyond-range indicator light 7117 to emit light and give an alarm, so that the operator may stop current movement immediately. The manual/automatic switching button 7118 is arranged to select a mode of controlling movement of the treatment table 40, and in an automatic mode, the preset position button 7111a may control the treatment table 40 and the treatment table positioning device 60 to move automatically within the simulated operating range, the positioning control module 73 automatically calculates movement trajectories of the linear axis 611 and the robot arm 612, while in a manual mode, movement of the treatment table under a set degree of freedom may be controlled manually, in the embodiment, a manual control button is only arranged on the hand-held controller 712. As to the emergency stop button 7119, when an accident occurs during movement of the treatment table, such as movement of the irradiated object, the emergency stop button 7119 may be pressed to stop the operation of the treatment table 40 and the treatment table positioning device 60, and after the accident is eliminated, the emergency stop button 7119 is released to continue to control movement of the treatment table. It should be understood that the buttons and switch buttons may also be replaced by other forms or have other functional settings. Different indicator lights may have different colors, and the indicator lights may also be replaced by other alarm indication such as buzzing.

Figure 6:
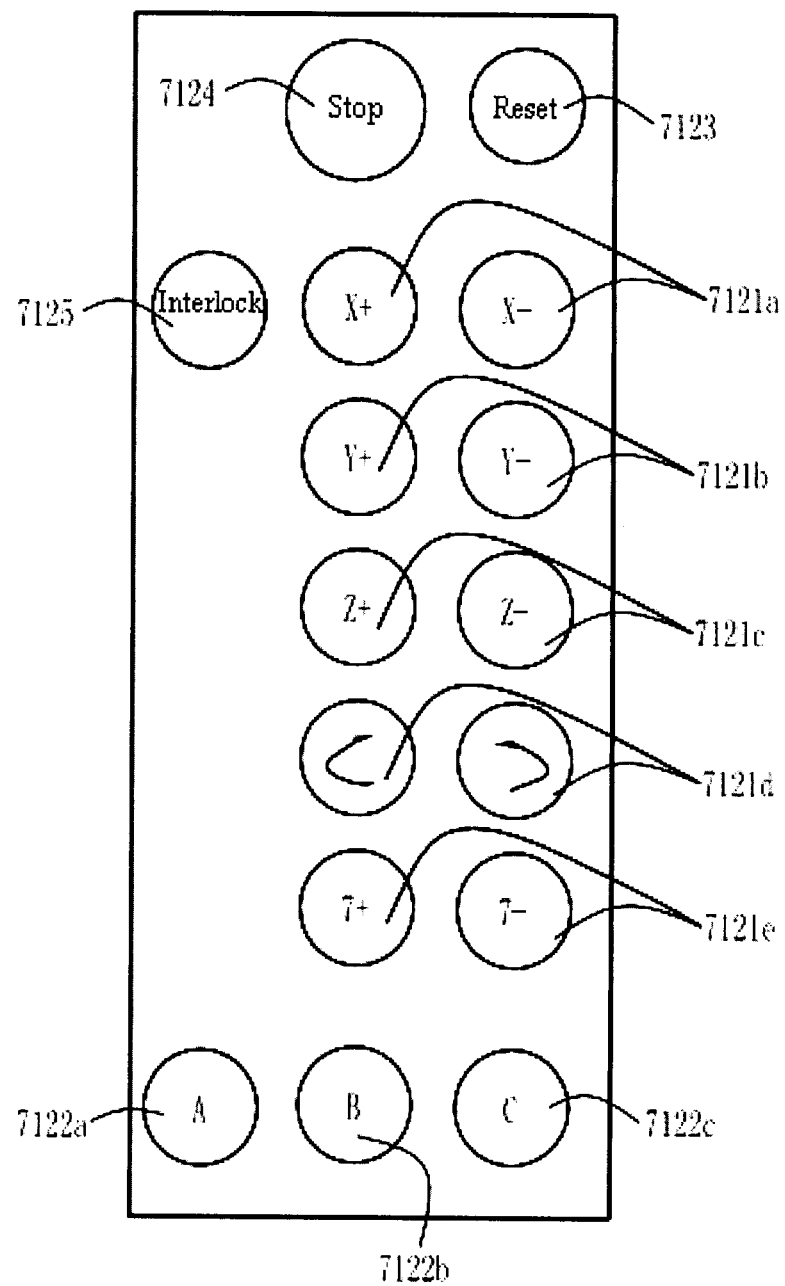
FIG. 6 is a schematic diagram of a user interface of a hand-held controller of a control device of a neutron capture therapy system according to an embodiment of the present disclosure.

The hand-held controller 712 facilitates observing movement state of the treatment table 40 in the irradiation room, and the operator may operate buttons on the controller 712 for adjustment while moving in the irradiation room for observation. As the preset positions A-G are preset according to a simulated irradiated object model without considering difference of the individual irradiated object, the position of the treatment table 40 may be further finely adjusted after reaching the preset position. As shown in FIG. 6, the hand-held controller 712 is provided with five sets of axis movement buttons which are shown respectively as axis movement buttons 7121a, 7121b, 7121c, 7121d and 7121e. The axis movement buttons 7121a, 7121b and 7121c control the preset reference point on the treatment table 40 to move along the X axis, Y axis and Z axis respectively. The axis movement button 7121d controls the treatment table 40 to rotate around the sixth pivot axis L6. The axis movement button 7121e controls the whole treatment table 40 and the whole treatment table positioning device 60 to move along the linear axis 611 (the seventh axis). An operating coordinate system XYZ of the treatment table and the treatment table positioning device takes the reference point of the irradiation room at a certain distance from the center of the beam outlet 25 in the direction of the neutron beam N as a coordinate origin. The hand-held controller 712 may also be provided with the same operation buttons or state indication as those in the fixed controller 711. In the embodiment, due to space limitation for the hand-held type to facilitate holding, three preset position buttons are provided, including: a preset position A (left face) button 7122a, a preset position B (right face) button 7122b, a preset position C (30 degrees to the left) button 7122c, a reset button 7123, and an emergency stop button 7124. The hand-held controller 712 is also provided with an interlock button 7125 as a misoperation prevention button. Only when the interlock button 7125 is pressed (unlocked), other buttons on the hand-held controller 712 will work, to prevent misoperation during holding. When the hand-held controller 712 is not used, the interlock button 7125 is locked, and at the moment, other buttons on the hand-held controller 712 will not work.

The man-machine interaction control interface 713 (not shown) may be a common computer software program interface which is arranged outside the irradiation room, for example, arranged in the control room, and may execute remote control, including execution of controlling various operations on the fixed controller 711 and the hand-held controller 712, such as the preset position button, the manual axis movement button, the reset button, the speed switching button, the manual/automatic switching button, the beyond-range alarm, the collision sensor triggering alarm, the continue-to-operate button, the emergency stop button, etc. It may also execute startup and shutdown of a device, fault or fault elimination display and a fault reset button; parameter setting, such as speed setting for each level; function shielding of the robot arm or treatment table anti-collision system, arranged to continue to perform positioning of the treatment table and treatment when an anti-collision facility is damaged, or debugging the system by an engineer; and I/O point state display. It may also execute beam control, radiation detection, etc.

A laser positioning device (not shown) is also arranged in the irradiation room 101, and arranged to determine the irradiation position of the beam. The treatment table positioning device 60 is operated to enable the irradiation position of the beam to be consistent with a mark made when the irradiated object 200 is simulated and positioned in the preparation room. There may also be a camera (not shown) to collect the position of the treatment table 40 and images of the irradiated object 200 in real time, the related data is transmitted to the system control module 72, and compared with information such as the treatment plan, and real-time adjustment is made or other treatment controls are performed according to the result of comparison. The system control module 72 may also receive other data information, such as data of the neutron generating device, data of the treatment plan, information of the irradiated object, etc., and control other devices such as the neutron generating device, etc.

In the embodiment, the concrete wall is a boron-containing barite concrete wall with a thickness of over 1 m and a density of 3 g/c.c., and the boron-containing concrete has better neutron absorption performance, which not only enhances the radiation shielding effect of the concrete, but also reduces exposure of metal materials in the concrete under neutrons. It should be understood that the concrete wall may have another thickness or density or be replaced by another material, and thicknesses, densities or materials of different parts of the concrete wall may also be different. It should be understood that the present invention may also be applied to other types of neutron irradiation systems, and may also be applied to other radiation irradiation systems, such as a proton therapy system, a heavy ion therapy system, etc., and at the moment, the neutron generating device may be replaced by another radiation generating device, and the materials of the concrete may be replaced as required. The treatment table may also be a carrying table of another irradiated object.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A radiation irradiation system comprising:
   a radiation generating device;
   a carrying table, wherein a beam generated by the radiation generating device irradiates an irradiated object on the carrying table; and
   a carrying table positioning device supporting the carrying table, wherein the carrying table positioning device comprises a positioning mechanism, the positioning mechanism comprises a linear axis along which the carrying table positioning device is horizontally movable, and an extending direction of the linear axis is parallel to an irradiation direction of beams generated by the radiation generating device.

2. The radiation irradiation system according to claim 1, wherein the positioning mechanism further comprises a robot arm arranged between the linear axis and the carrying table, the robot arm is provided to connect the carrying table with the linear axis, and the carrying table is movable together with the robot arm along the linear axis.

3. The radiation irradiation system according to claim 2, further comprising an irradiation room with a ceiling on which the linear axis is mounted and a floor towards which the whole robot arm extends.

4. The radiation irradiation system according to claim 2, wherein the linear axis comprises a fixed slide rail and a support seat connected with the robot arm and sliding along the slide rail, and a distance between a slide surface of the slide rail and the support seat and a center of a beam outlet of the radiation generating device in a direction perpendicular to the slide surface is less than 2 meters.

5. The radiation irradiation system according to claim 4, wherein the robot arm comprises a first arm fixedly connected with the support seat, a second arm pivotally connected with the first arm and defining a first pivot axis, a third arm pivotally connected with the second arm and defining a second pivot axis, a fourth arm pivotally connected with the third arm and defining a third pivot axis, a fifth arm pivotally connected with the fourth arm and defining a fourth pivot axis, a sixth arm pivotally connected with the fifth arm and defining a fifth pivot axis, and a seventh arm pivotally connected with the sixth arm and defining a sixth pivot axis.

6. The radiation irradiation system according to claim 5, wherein the seventh arm is fixedly connected with the carrying table, the second, third and fifth pivot axis are parallel to the slide surface, the fourth pivot axis is perpendicular to the third pivot axis, and the first and sixth pivot axis are perpendicular to the slide surface.

7. The radiation irradiation system according to claim 2, further comprising a control device controlling the carrying table positioning device and comprising a user interface, a system control module and a positioning control module, the user interface is connected with the system control module, and the system control module is connected with the positioning control module.

8. The radiation irradiation system according to claim 7, wherein the system control module transmits an instruction from the user interface to the positioning control module after receiving the instruction, and the positioning control module controls movement of the positioning mechanism.

9. The radiation irradiation system according to claim 7, wherein the positioning control module is capable of receiving position information of the positioning mechanism and transmitting it to the system control module, and the system control module controls the user interface to indicate the position information of the positioning mechanism.

10. The radiation irradiation system according to claim 7, wherein the carrying table positioning device further comprises a driving mechanism to drive movement of the linear axis and the robot arm, and the positioning control module is connected with the driving mechanism and controls the driving mechanism.

11. The radiation irradiation system according to claim 10, wherein an operating state or data of the driving mechanism is fed back to the system control module through the positioning control module, the system control module or the positioning control module controls the driving mechanism according to the operating state or data of the driving mechanism, and the system control module transmits the operating state or data of the driving mechanism to the user interface for state indication.

12. The radiation irradiation system according to claim 7, wherein a sensor is arranged on the carrying table or the carrying table positioning device and connected to the system control module, and the system control module receives a signal of the sensor, and then transmits an instruction to the positioning control module to control movement of the carrying table positioning device, and transmits the signal of the sensor to the user interface for state indication.

13. The radiation irradiation system according to claim 12, wherein the sensor is an anti-collision sensor arranged on the carrying table or the robot arm.

14. The radiation irradiation system according to claim 13, wherein the anti-collision sensor is a mechanical sensor, a photoelectric sensor, a radar sensor, an ultrasonic sensor or a laser rangefinder.

15. The radiation irradiation system according to claim 1, being a neutron capture therapy system, the radiation generating device comprises a neutron generating device and a beam shaping assembly, wherein the beam shaping assembly is configured to adjust quality of a neutron beam generated by the neutron generating device to a preset value, and the neutron beam generated by the neutron generating device passes through the beam shaping assembly to irradiate the irradiated object on the carrying table.

16. The radiation irradiation system of claim 15, wherein the neutron generating device comprises an accelerator and a target, a charged particle beam generated by acceleration of the accelerator interacts with the target to generate the neutron beam.

17. The radiation irradiation system of claim 15, wherein the beam shaping assembly comprises a reflector, a moderator, a thermal neutron absorber, a radiation shield and a beam outlet, the moderator decelerates neutrons generated from the target to an epithermal neutron energy region, the reflector surrounds the moderator and guides deviated neutrons back to the moderator to improve intensity of an epithermal neutron beam, the thermal neutron absorber is arranged to absorb thermal neutrons to avoid excessive dose for shallow normal tissues during treatment, and the radiation shield is arranged to shield neutrons and photons leaked from parts other than the beam outlet.

* * * * *